(12) United States Patent
Chihara et al.

(10) Patent No.: US 12,029,613 B2
(45) Date of Patent: Jul. 9, 2024

(54) DIAGNOSTIC ULTRASOUND APPARATUS (71) Applicant: Konica Minolta, Inc., Tokyo (JP)

(72) Inventors: Tatsushi Chihara, Tokyo (JP);
Takahiko Shiraishi, Kunitachi (JP);
Yasuhiro Nakamura, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 59 days.

(21) Appl. No.: 18/051,733

(22) Filed: Nov. 1, 2022

(65) Prior Publication Data

US 2023/0148030 A1 May 11, 2023

(30) Foreign Application Priority Data

Nov. 9, 2021 (JP) ................................ 2021-182511

(51) Int. Cl.
*A61B 8/00* (2006.01)
(52) U.S. Cl.
CPC .......... *A61B 8/4411* (2013.01); *A61B 8/4405* (2013.01); *A61B 8/4427* (2013.01)
(58) Field of Classification Search
CPC .... A61B 8/4405; A61B 8/4411; A61B 8/4427
See application file for complete search history.

(56) References Cited

U.S. PATENT DOCUMENTS

| 7,591,786 B2* | 9/2009 | Holmberg | A61B 8/56 |
| | | | 600/459 |
| 2002/0143256 A1* | 10/2002 | Wing | A61B 8/4433 |
| | | | 600/459 |
| 2009/0275835 A1* | 11/2009 | Hwang | A61B 8/4433 |
| | | | 600/443 |
| 2010/0056913 A1* | 3/2010 | Hirakui | A61B 8/4405 |
| | | | 600/437 |
| 2012/0265027 A1* | 10/2012 | Lee | A61B 8/4411 |
| | | | 600/301 |
| 2013/0218017 A1* | 8/2013 | Kim | A61B 8/462 |
| | | | 600/459 |
| 2014/0350357 A1* | 11/2014 | Lee | A61B 8/4477 |
| | | | 600/443 |

(Continued)

FOREIGN PATENT DOCUMENTS

WO 2013/046907 A1 4/2013

*Primary Examiner* — Colin T. Sakamoto
(74) *Attorney, Agent, or Firm* — LUCAS & MERCANTI, LLP (57) ABSTRACT

A diagnostic ultrasound apparatus includes a body, a display, a console, a probe port, a battery and a cart configured as separate units. The display, the console, the probe port and the battery are attachable to and detachable from the body. The body, the display and the console are attachable to and detachable from the cart. The body with the probe port and the battery attached, the display and the console are attached to the cart, thereby configuring the diagnostic ultrasound apparatus as a cart style. The display and the console are detached from the body with the probe port and the battery attached, thereby configuring the diagnostic ultrasound apparatus as a desktop style. The display, the console, the probe port and the battery are attached and connected to the body so as to be integrated, thereby configuring the diagnostic ultrasound apparatus as a hand-carry style.

11 Claims, 11 Drawing Sheets (56) References Cited

U.S. PATENT DOCUMENTS

| | | | | |
|---|---|---|---|---|
| 2015/0025389 A1* | 1/2015 | Murphy | ............... | A61B 8/4455 |
| | | | | 600/459 |
| 2015/0141835 A1* | 5/2015 | Nagase | ............... | A61B 8/4427 |
| | | | | 600/459 |
| 2015/0289841 A1* | 10/2015 | Brusacá | ............... | A61B 8/464 |
| | | | | 600/437 |
| 2019/0200958 A1* | 7/2019 | Shiraishi | ............... | F16M 11/00 |
| 2019/0298302 A1* | 10/2019 | Hong | ............... | A61B 8/5207 |
| 2019/0365352 A1* | 12/2019 | Song | ............... | A61B 8/4472 |

* cited by examiner

DIAGNOSTIC ULTRASOUND APPARATUS

CROSS-REFERENCE TO RELATED APPLICATIONS

The entire disclosure of Japanese Patent Application No. 2021-182511 filed on Nov. 9, 2021 is incorporated herein by reference in its entirety.

BACKGROUND

Technical Field

The present disclosure relates to a diagnostic ultrasound apparatus.

Description of the Related Art

In, for example, WO 2013/046907 A1, a cart for a portable diagnostic ultrasound device is disclosed. This cart enables a portable diagnostic ultrasound device to be used in a state of being placed on the cart and in a state of being removed from the cart.

SUMMARY

Usage environment of diagnostic ultrasound apparatuses varies depending on the situation of the site where they are used. Hence, diagnostic ultrasound apparatuses are required to have usability in a wide range of environment, which includes on a table, in a cart style, beside a bed, and on a wall.

The technique disclosed in WO 2013/046907 A1 does not allow a body of a portable diagnostic ultrasound device to be used with a display and a console thereof detached. Hence, the diagnostic ultrasound device cannot be used in a style suitable for the situation of the site where it is used, which is not user-friendly.

Objects of the present disclosure include providing a diagnostic ultrasound apparatus usable in a style suitable for the situation of the site where it is used.

According to an aspect of the present disclosure, there is provided a diagnostic ultrasound apparatus including a body, a display, a console, a probe port, a battery and a cart configured as separate units,
  wherein the display, the console, the probe port and the battery are attachable to and detachable from the body,
  wherein the body, the display and the console are attachable to and detachable from the cart,
  wherein (i) the body with the probe port and the battery attached, (ii) the display and (iii) the console are attached to the cart, thereby configuring the diagnostic ultrasound apparatus as a cart style,
  wherein the display and the console are detached from the body with the probe port and the battery attached, thereby configuring the diagnostic ultrasound apparatus as a desktop style, and
  wherein the display, the console, the probe port and the battery are attached and connected to the body so as to be integrated, thereby configuring the diagnostic ultrasound apparatus as a hand-carry style.

BRIEF DESCRIPTION OF THE DRAWINGS

The advantages and features provided by one or more embodiments of the present disclosure will become more fully understood from the detailed description given hereinbelow and the appended drawings that are given by way of illustration only, and thus are not intended as a definition of the limits of the present disclosure, wherein.

DETAILED DESCRIPTION OF EMBODIMENTS

Hereinafter, one or more embodiments of the present disclosure will be described with reference to the drawings. However, the technical scope of the present disclosure is not limited to the embodiments or illustrated examples.

Overall Configuration of Diagnostic Ultrasound Apparatus 100

FIG. 1A to FIG. 3B show examples of the external configuration of a diagnostic ultrasound apparatus 100 of the present disclosure.

The diagnostic ultrasound apparatus 100 is an apparatus that is used in an examination room or the like of a medical facility, such as a hospital, and includes a body 1, a probe port 2, a battery 3, a display 4, a console 5 and a cart 6 as units. These units of the diagnostic ultrasound apparatus 100 are configured as separate units. The probe port 2, the battery 3, the display 4 and the console 5 are attachable to and detachable from the body 1. The body 1, the display 4 and the console 5 are attachable to and detachable from the cart 6. The diagnostic ultrasound apparatus 100 can be converted into any of diagnostic ultrasound apparatuses of three styles, which are a cart-style diagnostic ultrasound apparatus shown in FIG. 1A and FIG. 1B, a desktop-style diagnostic ultrasound apparatus shown in FIG. 2, and a hand-carry-style diagnostic ultrasound apparatus shown in FIG. 3A and FIG. 3B, by combining (attaching/mounting) or separating (detaching/demounting) the units.

Configuration of Body 1

The body 1 controls the units of the diagnostic ultrasound apparatus 100, and thereby causes an ultrasound probe 7 attached to the probe port 2 to transmit and receive ultrasound to and from an object under examination (hereinafter "examination object"), generates ultrasound image data based on received ultrasound, performs image processing, performs display control, and so forth. That is, the body 1 transmits an electronic drive signal to the ultrasound probe 7 via the probe port 2 to cause the ultrasound probe 7 to transmit ultrasound to the not-shown examination object, and images the internal state of the examination object as ultrasound image data on the basis of an electronic received signal generated by the ultrasound probe 7 in accordance with reflected ultrasound from the inside of the examination object received by the ultrasound probe 7.

Some or all of functions that are performed by the body 1 can be realized by a hardware circuit(s), such as an integrated circuit. The integrated circuit is, for example, LSI (Large Scale Integration), and LSI may be called IC (Integrated Circuit), system LSI, super LSI or ultra LSI, depending on the degree of integration. The method for forming the integrated circuit is not limited to use of LSI, but a dedicated circuit or a general-purpose processor may be used, or an FPGA (Field Programmable Gate Array) or a reconfigurable processor that can reconfigure connection and setting of circuit cells in LSI may be used. Alternatively, some or all of the functions may be performed by software.

Figure 4A:
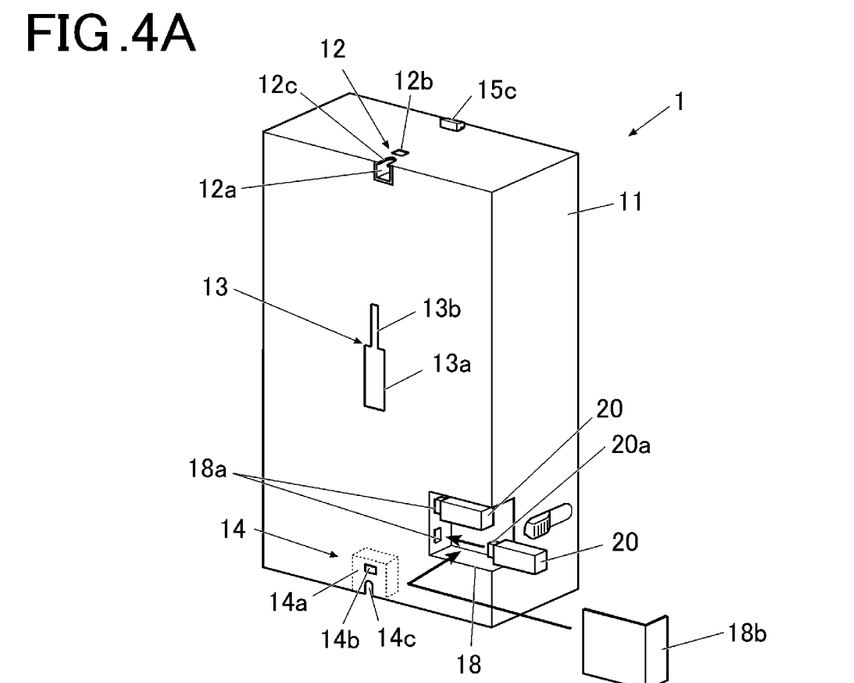
FIG. 4A is a front perspective view of a body.

FIG. 4A is a front perspective view of the body 1.

As shown in FIG. 4A, the front surface of a case 11 of the body 1 is provided with a display connection part 12 for connecting with the display 4, a cart connection part 13 for connecting with the cart 6, and a console connection part 14 for connecting with the console 5.

The display connection part 12 is, for example, provided at the top of the front surface of the body 1, and has a connector 12a, a latch receiving hole 12b and a button fit part 12c to electrically and mechanically connect the display 4 and the body 1.

The connector 12a is a connector for connecting with a connector 42a (shown in FIG. 8) of the display 4, a connector 92a (shown in FIG. 8) of a display cable 9 or a connector 63c (shown in FIG. 10) of the cart 6. The display cable 9 (shown in FIG. 8) is a cable for connecting the display 4 and the body 1, and has a connection part 91 having the same structure as the display connection part 12 and a connection part 92 having the same structure as a connection part 42 of the display 4.

The latch receiving hole 12b engages with a latch 42b (shown in FIG. 8), a latch 92b (shown in FIG. 8) or a latch 63d (shown in FIG. 10) when the connector 42a, the connector 92a or the connector 63c is inserted in the connector 12a, thereby fixing the display 4, the display cable 9 or the cart 6 to the body 1.

The button fit part 12c fits with an unlatch button 42c (shown in FIG. 8), an unlatch button 92c (shown in FIG. 8) or an unlatch button 63e (shown in FIG. 10) when the connector 42a, the connector 92a or the connector 63c is inserted in the connector 12a.

The cart connection part 13 is, for example, provided at the center of the front surface of the body 1 for attaching (fixing) the body 1 to the cart 6. The cart connection part 13 has openings 13a, 13b. The opening 13a is larger than a guide 63a (shown in FIG. 10) of a support pillar 63 of the cart 6. The opening 13b is narrower than the guide 63a, extends upward, and is provided above the opening 13a so as to communicate with the opening 13a. The body 1 can be attached to the cart 6 by inserting the guide 63a into the opening 13a and thereafter sliding the body 1 downward with both ends (edges) of the opening 13b being fitted in grooves of the guide 63a.

The console connection part 14 is, for example, provided at the bottom of the front surface of the body 1, and has a connector 14a, a latch receiving hole 14b and a button fit part 14c to electrically and mechanically connect the console 5 and the body 1.

The connector 14a is a connector for connecting with a connector 52a (shown in FIG. 9A) of the console 5, a connector 81a (shown in FIG. 9A) of a console cable 8 or a connector 64a (shown in FIG. 10) of the cart 6. The console cable 8 (shown in FIG. 9A) is a cable for connecting the console 5 and the body 1, and has a connection part 81 having the same structure as a connection part 52 of the console 5 and a connection part 82 having the same structure as the console connection part 14.

The latch receiving hole 14b engages with a latch 52b (shown in FIG. 9A), a latch 81b (shown in FIG. 9A) or a latch (not shown) of the cart 6 when the connector 52a, the connector 81a or the connector 64a is inserted in the connector 14a, thereby fixing the console 5, the console cable 8 or the cart 6 to the body 1.

The button fit part 14c fits with an unlatch button 52c (shown in FIG. 9A), an unlatch button 81c (shown in FIG. 9A) or an unlatch button (not shown) of the cart 6 when the connector 52a, the connector 81a or the connector 64a is inserted in the connector 14a.

Figure 4B:
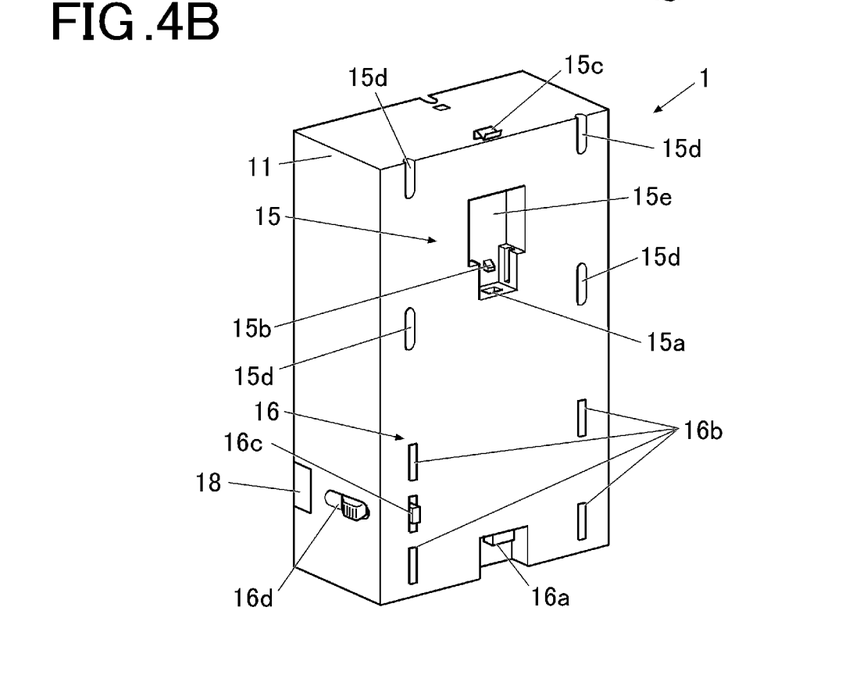
FIG. 4B is a rear perspective view of the body.

FIG. 4B is a rear perspective view of the body 1.

As shown in FIG. 4B, the rear surface of the case 11 of the body 1 is provided with a port connection part 15 for connecting with the probe port 2 and a battery connection part 16 for connecting with the battery 3.

The port connection part 15 electrically and mechanically connects the probe port 2 and the body 1. The port connection part 15 is, for example, provided at the upper side of the rear surface of the body 1, and has a connector 15a, a latch 15b, an unlatch button 15c and rotation stops 15d. The latch 15b is disposed in a recess 15e that fits with a projection 23e (shown in FIG. 6B) of a body connection part 23 of the probe port 2. The connector 15a is disposed at the lower part of the recess 15e.

The connector 15a is a connector for connecting with a connector 23a (shown in FIG. 6B) of the probe port 2.

The latch 15b engages with a latch receiving hole 23b (shown in FIG. 6B) of the probe port 2 when the connector 23a of the probe port 2 is inserted in the connector 15a, thereby fixing the probe port 2 to the body 1.

The unlatch button 15c disengages the latch 15b from the latch receiving hole 23b of the probe port 2 by being pressed. Thus, the unlatch button 15 can remove the connector 23a from the connector 15a.

The rotation stops 15d are concave, and fit with convex rotation stops 23d of a case 21 of the probe port 2, thereby preventing the case 21 from rotating.

The battery connection part 16 electrically and mechanically connects the battery 3 and the body 1. The battery connection part 16 is, for example, provided at the lower side of the rear surface of the body 1, and has a connector 16a, battery hook receptacles 16b, a stopper 16c and a stopper fixing/unfixing button 16d.

The connector 16a is a connector for connecting with a connector 32a (shown in FIG. 7) of the battery 3.

Figure 5:
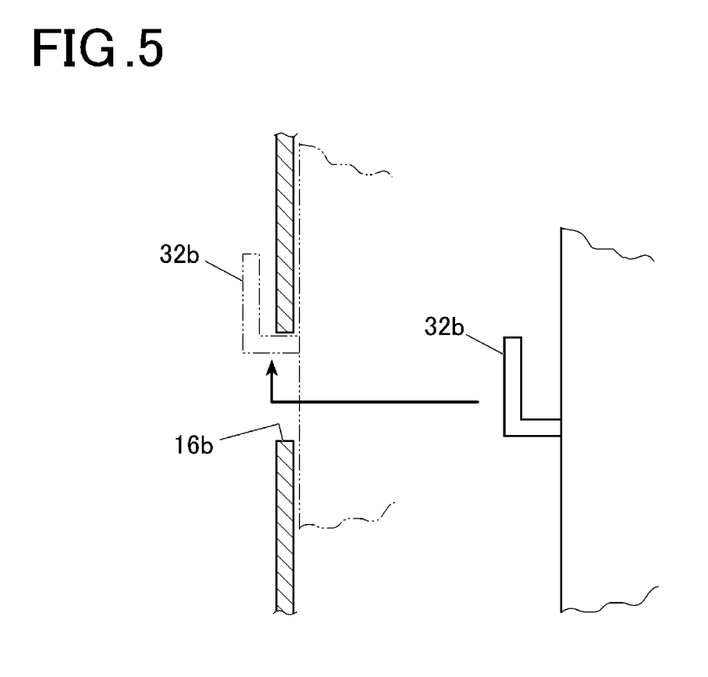
FIG. 5 schematically shows engagement of a hook of a battery with a battery hook receptacle of the body.

The battery hook receptacles 16b are openings as shown in FIG. 5. When hooks 32b of the battery 3 are inserted into the battery hook receptacles 16b, and the connector 32a is inserted into the connector 16a, the battery hook receptacles 16b can engage with the hooks 32b.

The stopper 16c protrudes from the case 11 of the body 1 when the stopper fixing/unfixing button 16d is slid rightward, and is housed in the case 11 of the body 1 when the stopper fixing/unfixing button 16d is slid leftward. When the stopper 16c fits with a stopper receptacle 32c (shown in FIG. 7) of the battery 3, the battery 3 can be fixed to the body 1.

Figure 1A:
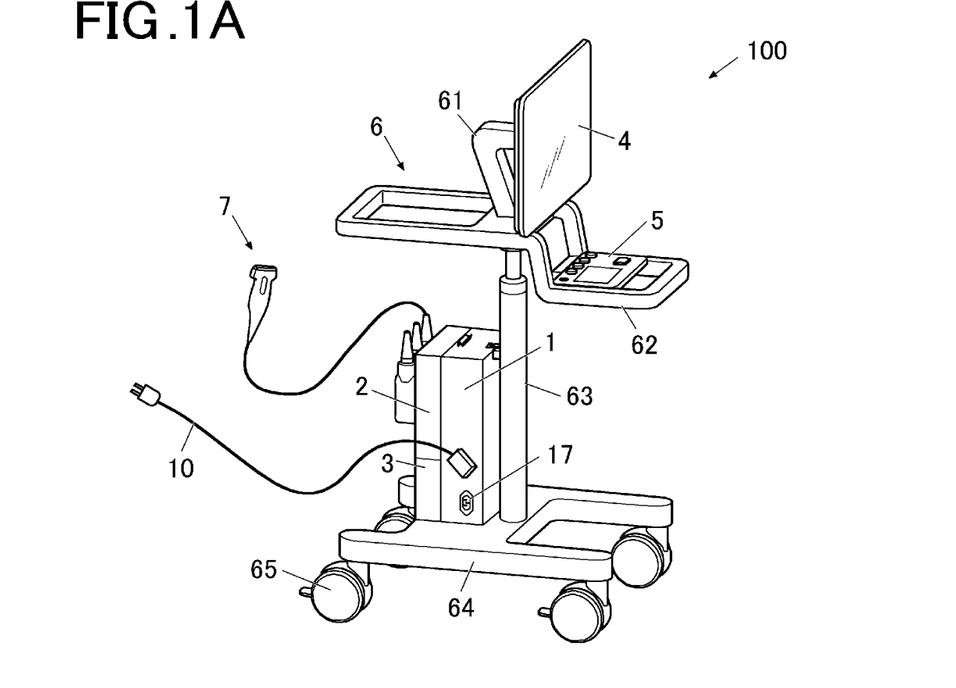
FIG. 1A is a side view of a cart-style diagnostic ultrasound apparatus.

As shown in FIG. 1A, the side surface of the body 1 is provided with a connector 17 into which a power cable 10 that connects to an AC power source is inserted.

As shown in FIG. 4A, the body 1 has a storage 18 for storing wireless communication units 20 for wireless communication by WiFi®, Bluetooth® or the like. The storage 18 is formed by denting the case 11 (the front surface and the side surface thereof in this embodiment) of the body 1. The storage 18 has versatile connectors 18a for connecting with connectors 20a of the wireless communication units 20. The storage 18 is formed such that the wireless communication units 20 can fit in the depression of the storage 18 with the connectors 20a of the wireless communication units 20 inserted in the versatile connectors 18a. The storage 18 further has a lid 18b, and can house the wireless communication units 20 in the body 1 by being closed/covered with the lid 18b, so that the wireless communication units 20 can be easily taken out therefrom. When the connector(s) 20a of the wireless communication unit(s) 20 are inserted into the versatile connector(s) 18a, the body 1 can wirelessly connect, via the wireless communication unit(s) 20, to external apparatus(es) that are capable of wireless communication.

Thus, storing the wireless communication units 20 in the storage 18 can prevent the wireless communication units 20 from protruding from the body 1 and thereby can prevent, for example, the wireless communication units 20 from being caught by something or water from being spilled on the wireless communication units 20. The above also makes it possible to easily take out the wireless communication units 20 from the body 1 and replace them with others when the standard for wireless communication units 20 is updated or when wireless communication units 20 meeting the standard of another country are needed.

Configuration of Probe Port 2

The probe port 2 is a device that is attached to the body 1 and electrically connects the ultrasound probe 7 to the body 1. The ultrasound probe 7 (shown in FIG. 1B) has a probe 71, a probe connector 72 and a cable 73, and transmits ultrasound (transmissive ultrasound) into the examination object, such as the body of a patient, and receives reflected waves of ultrasound reflected in the examination object (reflected ultrasound or echo).

Figure 6A:
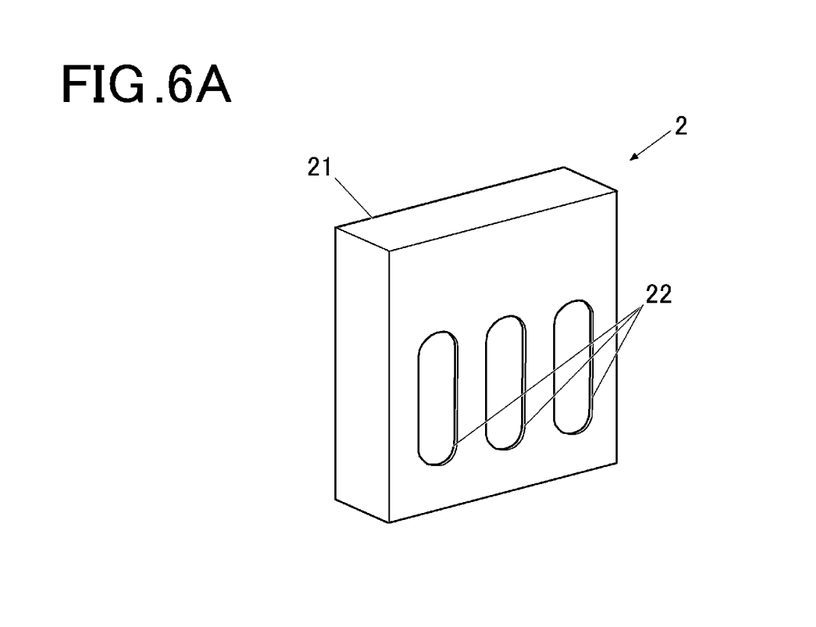
FIG. 6A is a front perspective view of a probe port.

FIG. 6A is a front perspective view of the probe port 2.

As shown in FIG. 6A, the case 21 of the probe port 2 is in the shape of a cuboid having square front and rear surfaces, and the front surface is provided with a plurality of (three in this embodiment) ports 22. Each port 22 is configured such that the probe connector 72 of the ultrasound probe 7 is connectable, to connect the ultrasound probe 7 to the body 1 (shown in FIG. 1B, FIG. 3B, FIG. 11, etc.).

Figure 6B:
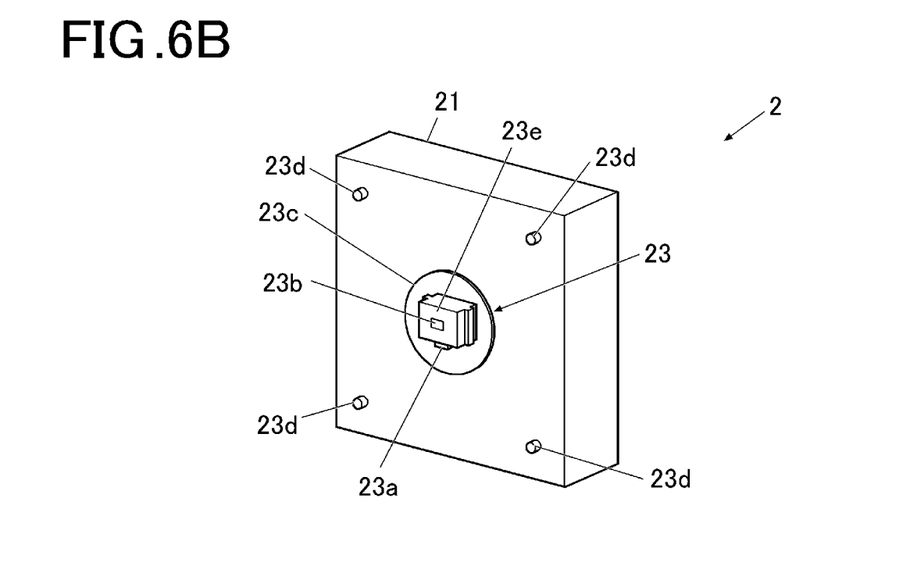
FIG. 6B is a rear perspective view of the probe port.

FIG. 6B is a rear perspective view of the probe port 2. As shown in FIG. 6B, the rear surface of the case 21 of the probe port 2 is provided with the body connection part 23.

The body connection part 23 has the connector 23a, the latch receiving hole 23b, the rotation stops 23d, the projection 23e, and a disk (disc) 23c. The latch receiving hole 23b is provided in the projection 23e that fits with the recess 15e of the body 1. The connector 23a is disposed under and on the bottom of the projection 23e.

The connector 23a is a connector for connecting with the connector 15a (shown in FIG. 4B) of the body 1.

The latch receiving hole 23b engages with the latch 15b of the body 1 when the connector 23a is inserted in the connector 15a, thereby fitting the probe port 2 to the body 1.

The projection 23e is fixed to the disk 23c that is attached parallel to the case 21 of the probe port 2 via a not-shown shaft disposed at the center of the rear surface of the case 21. This shaft is attached to the center of the disk 23c, and the disk 23c and the case 21 are capable of relative rotation on the shaft. The projection 23e is provided with the connector 23a and the latch receiving hole 23b. The orientation of the ports 22 can be changed (shown in FIG. 3B and FIG. 11) by rotating the case 21 of the probe port 2 relative with the disk 23c in units of 90 degrees with the connector 23a inserted in the connector 15a and the projection 23e fitted in the recess 15e. More specifically, the orientation of the ports 22 in the longer direction thereof can be changed to any of four directions, namely, to the upward direction or the downward direction (the side of the probe connector 72 closer to the probe 71 faces the upward direction or the downward direction) or the rightward direction or the leftward direction (the side of the probe connector 72 closer to the probe 71 faces the rightward direction or the leftward direction).

The rotation stops 23d are convex, and fit with the concave rotation stops 15d of the body 1, thereby preventing the case 21 of the probe port 2 from rotating, and fixing the orientation of the ports 22 accordingly.

In order that the orientation of the ports 22 can be changed, the probe port 2 may be configured such that the projection 23e, which is provided with the connector 23a and the latch receiving hole 23b, is fixed to the case 21, and the ports 22 are attached to the case 21 so as to be rotatable.

Configuration of Battery 3

The battery 3 is attached to the body 1, and is charged by a charging circuit of the body 1 while the power cable 10 connected to the body 1 is plugged in an outlet of the AC power source (commercial power source), and supplies power to the body 1 under the control of the body 1 while the power cable 10 connected to the body 1 is unplugged from the outlet of the AC power source.

Figure 7:
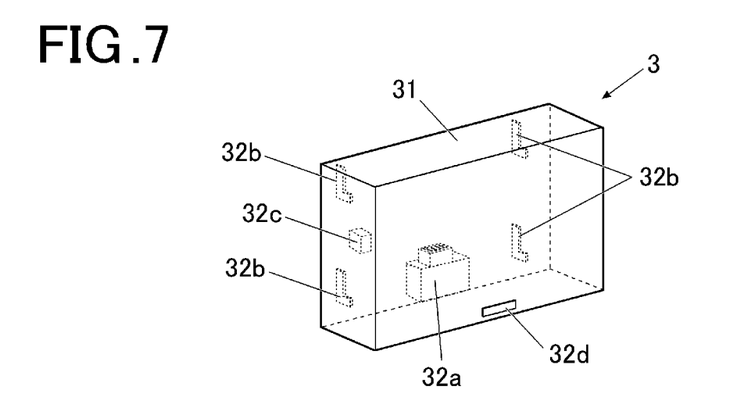
FIG. 7 is a front perspective view of the battery.

FIG. 7 is a front perspective view of the battery 3. As shown in FIG. 7, the battery 3 has the connector 32a, the hooks 32b and the stopper receptacle 32c on the rear surface of the case 31, and has a fixation latch receptacle 32d on the front surface of the case 31.

The connector 32a is a connector for connecting with the connector 16a (shown in FIG. 4B) of the body 1.

The hooks 32b are L-shaped and, as shown in FIG. 5, engage with the battery hook receptacles 16b of the body 1, thereby attaching the battery 3 to the body 1.

The stopper receptacle 32c is concave, and fits with the stopper 16c of the body 1, thereby fixing the battery 3 to the body 1.

The fixation latch receptacle 32d engages with a fixation latch 64b (shown in FIG. 10) of the cart 6, thereby fixing, to the cart 6, the body 1 with the battery 3 attached.

As described above, the battery 3 is attachable to and detachable from the body 1. This makes it possible to appropriately replace the battery 3 attached to the body 1 with a battery 3 of a different capacity according to the user's needs, for example, with a large-capacity battery 3.

Configuration of Display 4

The display 4 is constituted of an LCD (Liquid Crystal Display) or the like, and displays ultrasound images and so forth on the basis of control signals input from the body 1.

Figure 8:
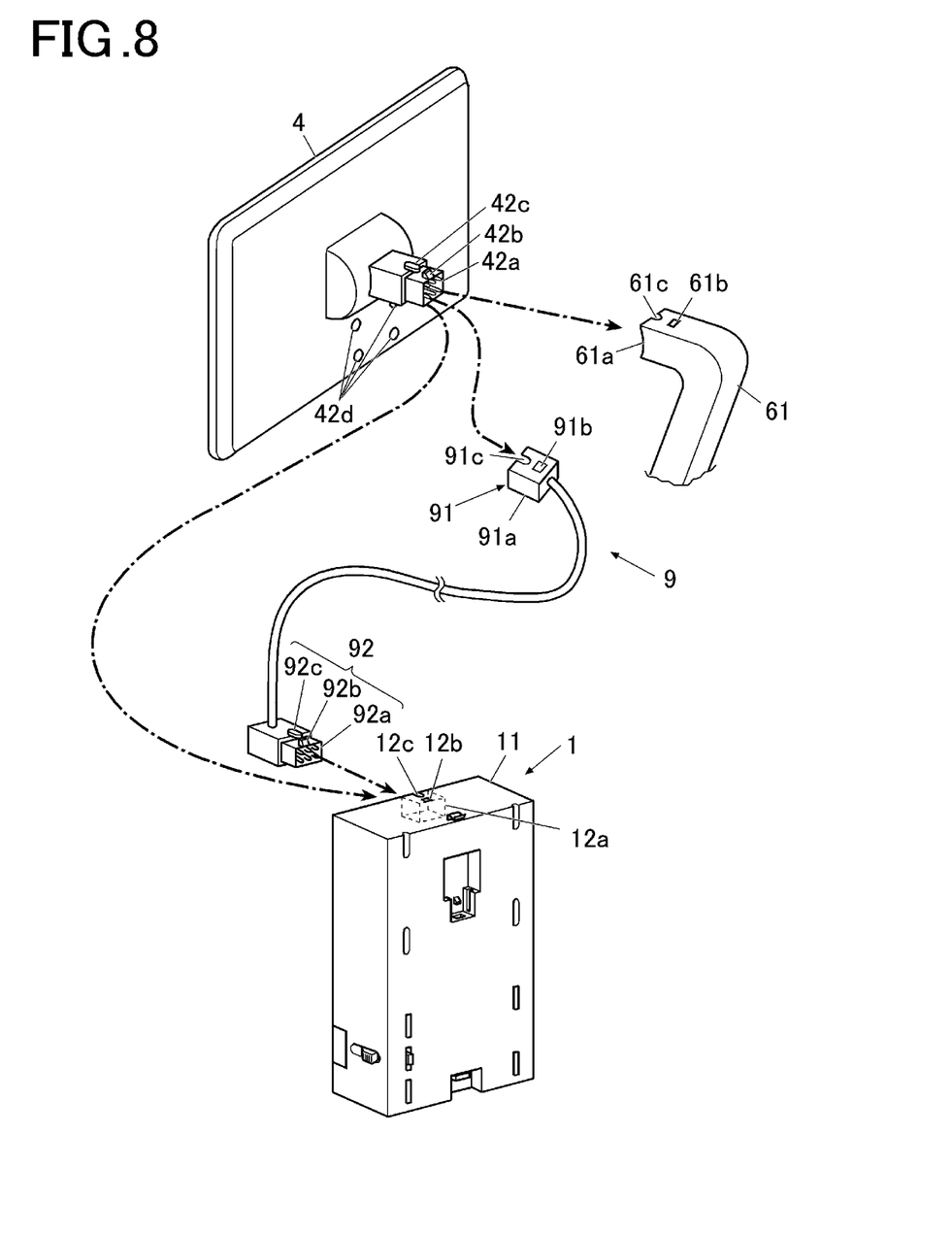
FIG. 8 is a rear perspective view of a display and schematically shows connection thereof to other units.

FIG. 8 is a rear perspective view of the display 4 and schematically shows connection of the display 4 to other units. As shown in FIG. 8, the rear surface of the display 4 is provided with the connector 42a, the latch 42b, the unlatch button 42c and screw holes 42d. Further, the display 4 has a not-shown battery.

The connector 42a is a connector for connecting with the connector 12a (shown in FIG. 4A) of the body 1, a connector 91a of the display cable 9 or a connector 61a disposed in a display arm 61 of the cart 6.

The latch 42b engages with the latch receiving hole 12b, a latch receiving hole 91b or a latch receiving hole 61b when the connector 42a is inserted in the connector 12a of the body 1, the connector 91a or the connector 61a, thereby fixing the display 4 to the body 1, the display cable 9 or the display arm 61.

The unlatch button 42c disengages the latch 42b from the latch receiving hole 12b, 91b or 61b by being pressed. Thus, the unlatch button 42c can remove the connector 42a from the connector 12a, 91a or 61a.

The screw holes 42d are in conformity with, for example, VESA standard, and enable the display 4 to be attached to a common wall mount or stand.

Configuration of Console 5

The console 5 has a push button, an encoder (rotary knob), a lever switch, a joystick, a trackball, a keyboard, a multi-function switch combining two or more of these, and/or the like, and receives operations input by an operator and outputs information on the operations to the body 1.

Figure 9A:
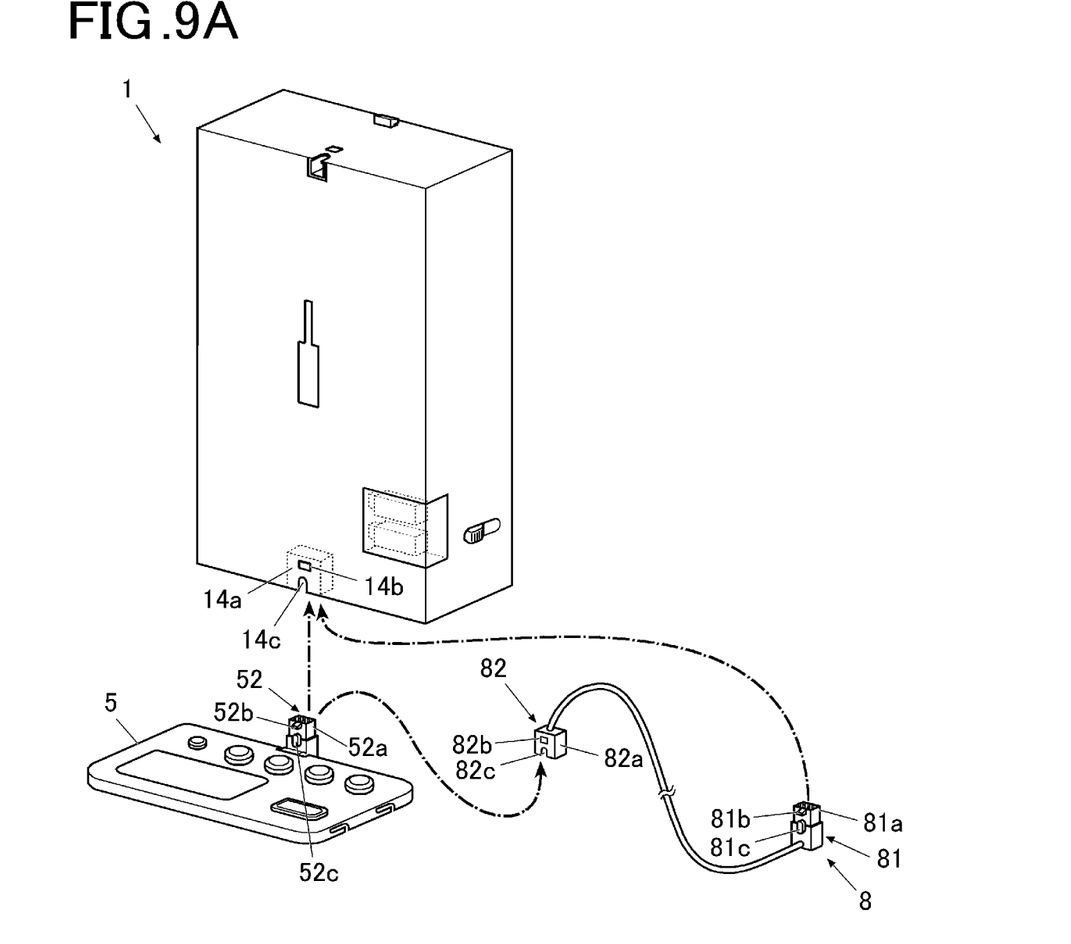
FIG. 9A is a top perspective view of a console and schematically shows connection thereof to the body.
Figure 9B:
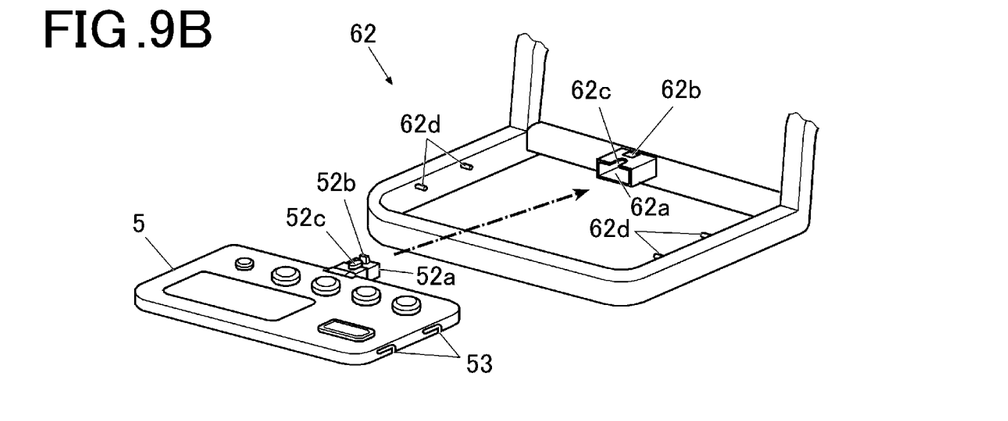
FIG. 9B is a top perspective view of the console and schematically shows connection thereof to a cart.
Figure 10:
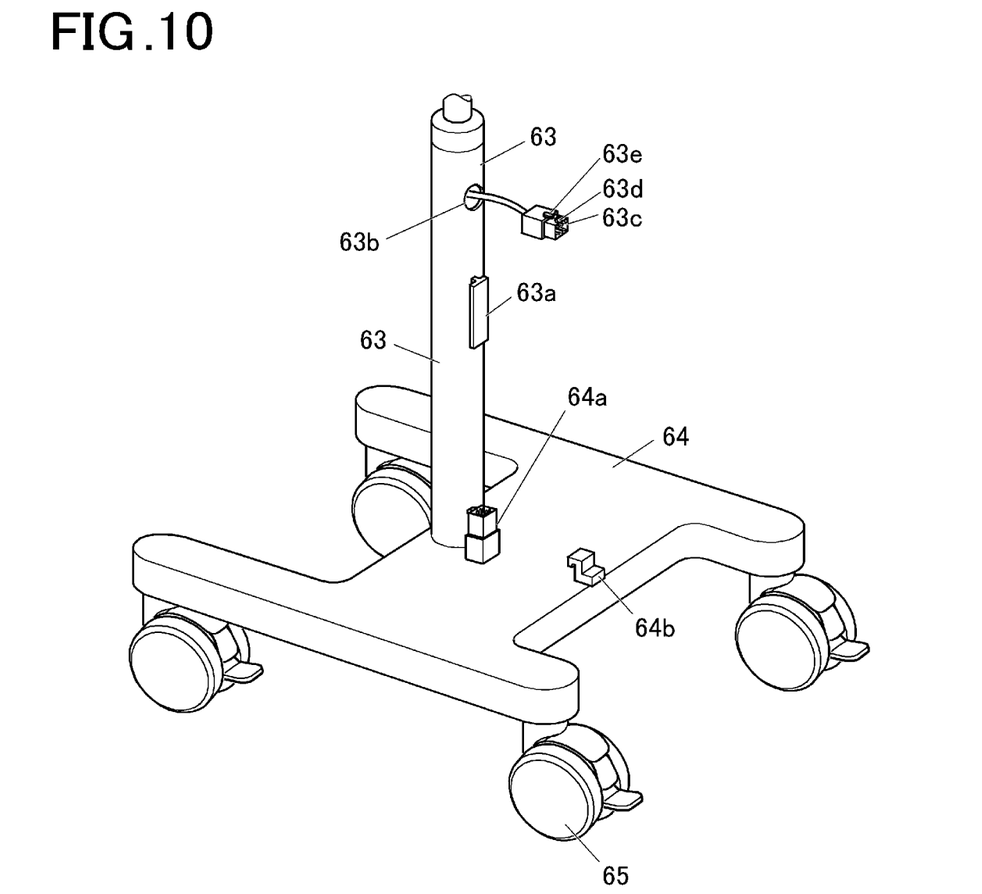
FIG. 10 schematically shows a part of the cart connecting with the body.

FIG. 9A is a perspective view of the console 5 and schematically shows connection of the console 5 to the body 1. FIG. 9B is a perspective view of the console 5 and schematically shows connection of the console 5 to the cart 6. As shown in FIG. 9A or FIG. 9B, the end part of the console 5 facing the body 1 or the cart 6 is provided with the connection part 52 having the connector 52a, the latch 52b and the unlatch button 52c. The connection part 52 is attached to the console 5 so as to be rotatable around the longer direction of the console 5 as an axis, so that the orientation of the connector 52a can be changed. The right surface and the left surface of the console 5 are provided with pin receptacles 53. Further, the console 5 has a not-shown battery.

The connector 52a is a connector for connecting with the connector 14a of the body 1, a connector 82a of the console cable 8 or a connector 62a of a console placement part 62 of the cart 6.

The latch 52b engages with the latch receiving hole 14b, a latch receiving hole 82b or a latch receiving hole 62b when the connector 52a is inserted in the connector 14a, the connector 82a or the connector 62a, thereby fixing the console 5 to the body 1, the console cable 8 or the cart 6.

The unlatch button 52c disengages the latch 42b from the latch receiving hole 14b, 82b or 62b by being pressed. Thus, the unlatch button 52 can remove the connector 52a from the connector 14a, 82a or 62a.

The pin receptacles 53 engage with console receiving pins 62d of the cart 6, thereby attaching the console 5 to the cart 6.

As described above, the console 5 is attachable to and detachable from the body 1. There is a demand to change the layout of the console 5 depending on a hospital department or the like. Preparation of consoles 5 with different layouts can appropriately change the layout of the console 5 that is attached to the body 1, the display 4 or the like, according to the user's needs.

Configuration of Cart 6

Figure 1B:
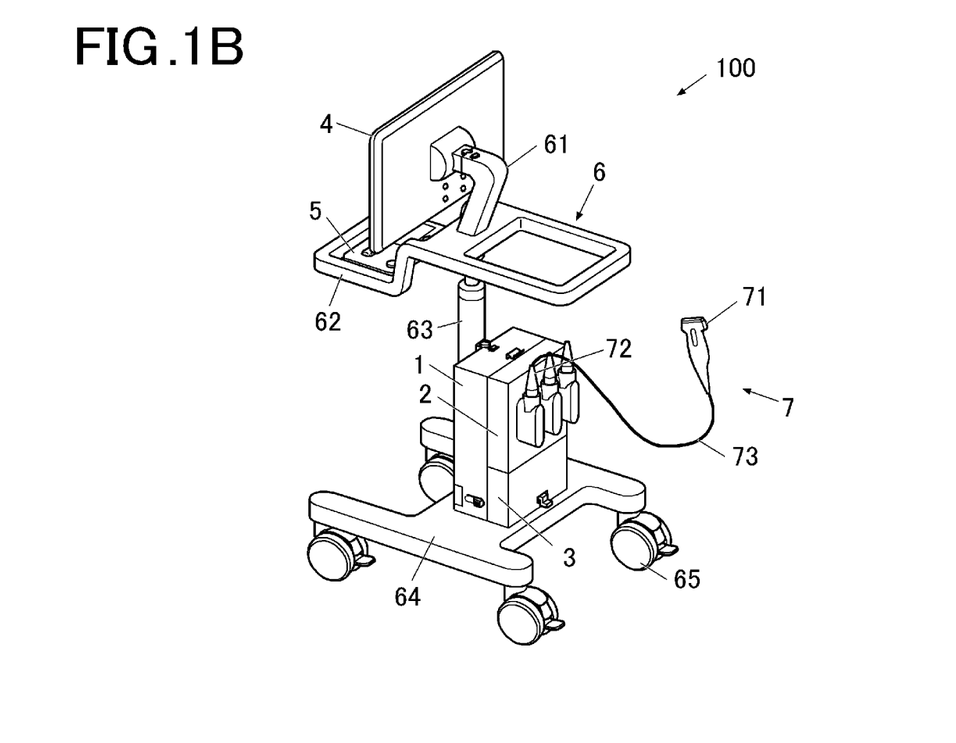
FIG. 1B is a rear perspective view of the cart-style diagnostic ultrasound apparatus.

As shown in FIG. 1A and FIG. 1B, the cart 6 has, for example, the display arm 61, the console placement part 62, the support pillar 63, a body placement part 64 and castors 65, and can be moved together with the units of the diagnostic ultrasound apparatus 100 mounted/attached thereon/thereto.

As shown in FIG. 8, the display arm 61 has the connector 61a, the latch receiving hole 61b and a button fit part 61c, and connects to and holds the display 4.

The connector 61a is a connector for connecting with the connector 42a of the display 4.

The latch receiving hole 61b engages with the latch 42b, thereby fixing the display 4 to the display arm 61.

The button fit part 61c fits with the unlatch button 42c.

As shown in FIG. 9B, the console placement part 62 has the connector 62a, the latch receiving hole 62b, the console receiving pins 62d and a button fit part 62c, and connects to and holds the console 5.

The connector 62a is a connector for connecting with the connector 52a of the console 5.

The latch receiving hole 62b engages with the latch 52b, thereby fixing the console 5 to the cart 6.

The button fit part 62c fits with the unlatch button 52c.

The console receiving pins 62d are convex, and engage with the pin receptacles 53 that are grooves provided in the side surfaces of the console 5, thereby holding the console 5.

As shown in FIG. 10, the support pillar 63 is provided with the guide 63a for attaching the body 1 to the support pillar 63. The guide 63a fits in the opening 13b of the cart connection part 13 of the body 1, thereby fixing the body 1 to the support pillar 63. The support pillar 63 is also provided with an opening 63b for pulling out, from the support pillar 63, a cable that connects the connector 61a (shown in FIG. 8) of the display arm 61 and the connector 63c (which has the same structure as the connector 42a of the display 4). Hence, connecting the connector 42a of the display 4 to the connector 61a and connecting the connector 63c to the connector 12a can electrically connect the display 4 and the body 1.

The body placement part 64 is a body rest where the body 1 is placed, and has the connector 64a, the fixation latch 64b and the castors 65. The connector 64a has the same structure as the connector 52a of the console 5, and is connected to the connector 62a shown in FIG. 9B by a not-shown cable. Hence, connecting the connector 64a to the connector 14a of the body 1 can electrically connect the console 5 and the body 1. The fixation latch 64b engages with the latch receptacle 32d provided in the battery 3, thereby fixing, to the cart 6, the body 1 with the battery 3 attached.

The diagnostic ultrasound apparatus 100 having the units thus configured can change its style to any of three styles, which are the cart type, the desktop type and the hand-carry type.

Styles of Diagnostic Ultrasound Apparatus 100

The body 1 with the probe port 2 and the battery 3 attached is attached to the body placement part 64 of the cart 6, the display 4 is attached to the display arm 61 of the cart 6, and the console 5 is attached to the console placement part 62 of the cart 6, so that the cart-type/style diagnostic ultrasound apparatus 100 shown in FIG. 1A and FIG. 1B can be configured.

Figure 2:
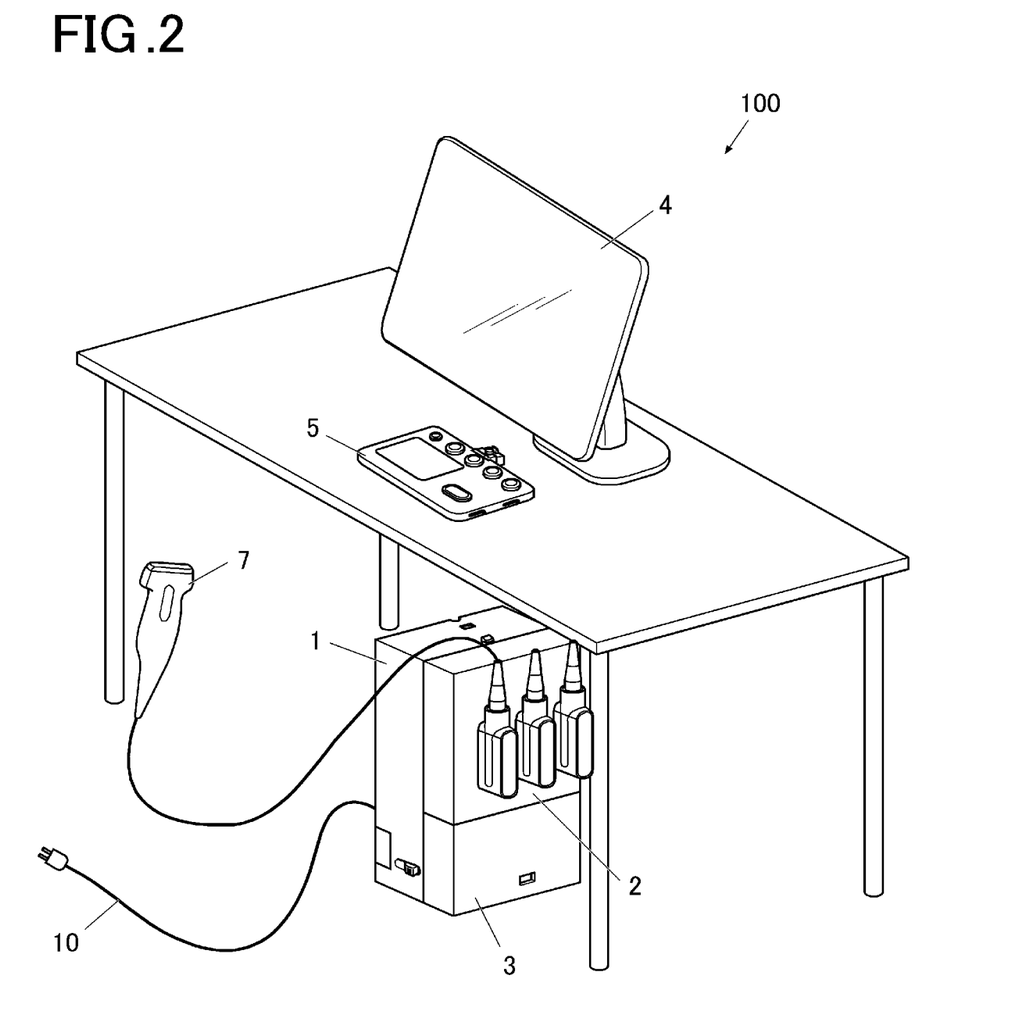
FIG. 2 is a perspective view of a desktop-style diagnostic ultrasound apparatus.

The probe port 2 and the battery 3 are attached to the body 1, and the display 4 and the console 5 are detached from the body 1 and connected to the body 1 via the display cable 9 and the console cable 8, respectively, so that the desktop-type/style diagnostic ultrasound apparatus 100 shown in FIG. 2 can be configured.

The display 4 and the console 5 may be provided with wireless communication units, so that the display 4 and the console 5 can be connected to the body 1 wirelessly.

Figure 3A:
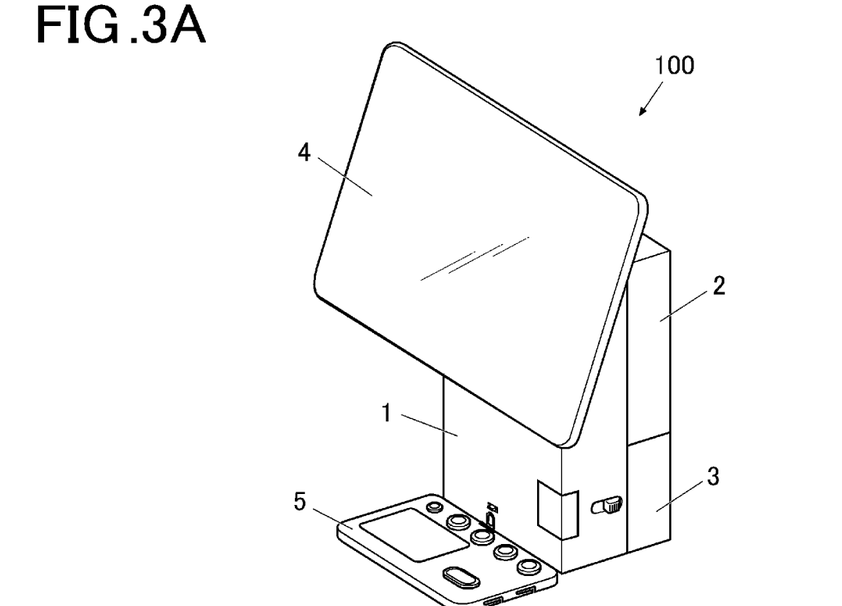
FIG. 3A is a front perspective view of a hand-carry-style diagnostic ultrasound apparatus.
Figure 3B:
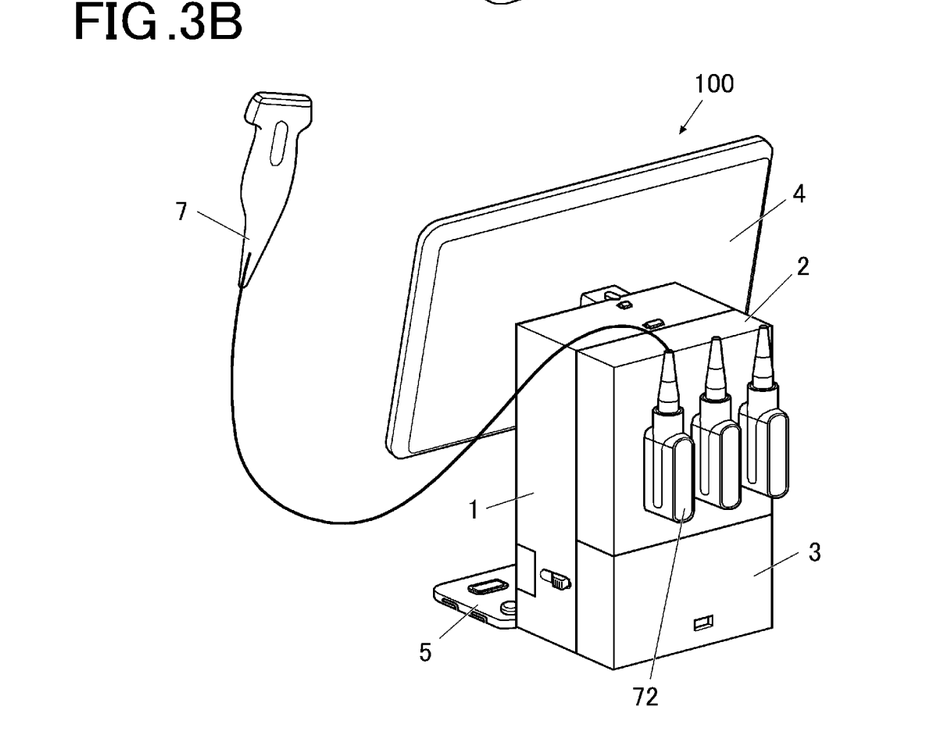
FIG. 3B is a rear perspective view of the hand-carry-style diagnostic ultrasound apparatus.

The probe port 2 and the battery 3 are attached to the body 1 and also the display 4 and the console 5 are attached to the body 1 so as to be all integrated, so that the hand-carry-type/style diagnostic ultrasound apparatus 100 shown in FIG. 3A and FIG. 3B can be configured.

Thus, the diagnostic ultrasound apparatus 100 can freely change its style to any of three styles, which are the cart style, the desktop style and the hand-carry style. The diagnostic ultrasound apparatus 100 can therefore be used in a style suitable for the situation of the site where it is used, for example, in a style suitable for being used on a table, during a round of visits, beside a bed, or on a wall.

Figure 11:
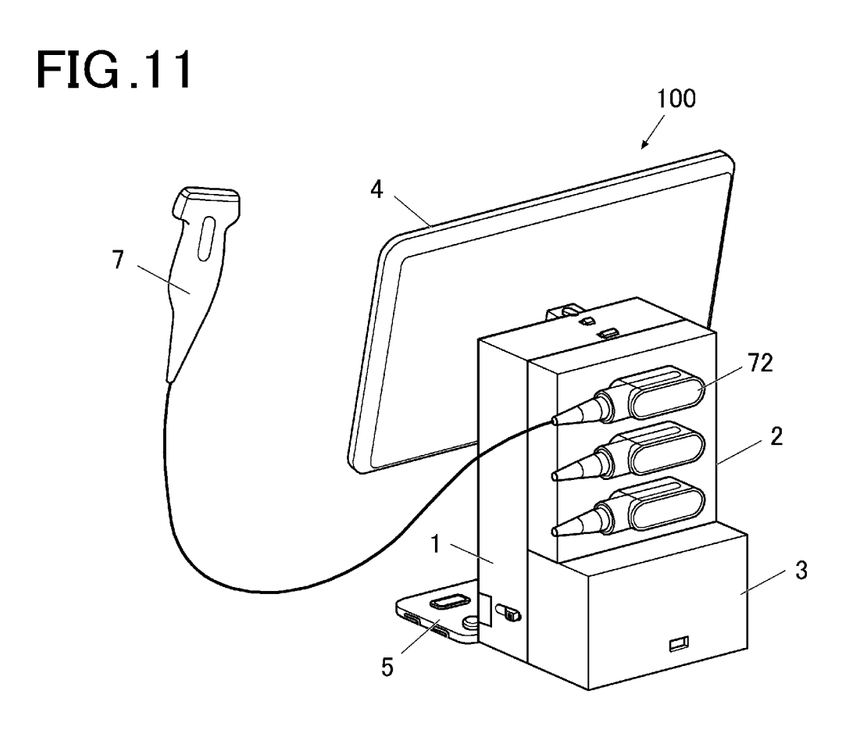
FIG. 11 shows an example in which the probe port and the battery are attached to the body with the orientation of the probe port changed and the capacity of the battery changed.

Further, as described above, the probe port 2 can be attached to the body 1 with the orientation of the ports 22 changed as shown in FIG. 11. This makes it possible to change the orientation of the probe connector 72 of the probe connector 72 to a direction for the user to easily use the ultrasound probe 7, which improves usability (user-friendliness) of the diagnostic ultrasound apparatus 100.

Further, as described above, the battery 3 and the console 5 can be replaced with one having another capacity and one having another layout, respectively. Hence, as shown in FIG. 11, the capacity of the battery 3 and the layout of the console 5 can be changed according to the user's needs or the department's needs.

Although one or more embodiments of the present disclosure have been described above, those described in the embodiments are not limitations but examples of the diagnostic ultrasound apparatus of the present disclosure.

Further, the detailed configuration and operation of each device/unit constituting the diagnostic ultrasound apparatus can be appropriately modified without departing from the scope of the present disclosure.

Although one or more embodiments or the like of the present disclosure have been described and illustrated in detail, the disclosed embodiments or the like are made for purposes of not limitation but illustration and example only. The scope of the present invention should be interpreted by terms of the appended claims.

What is claimed is:

1. A diagnostic ultrasound apparatus comprising a body, a display, a console, a probe port, a battery and a cart configured as separate units,
wherein the display, the console, the probe port and the battery are attachable to and detachable from the body,
wherein the body, the display and the console are attachable to and detachable from the cart,
wherein the body, the display, the console, the probe port, the battery, and the cart are configurable in a plurality of configurations including:
a cart style configuration in which (i) the body with the probe port and the battery attached, (ii) the display and (iii) the console are attached to the cart,
a desktop style configuration in which the body, the display, the console, the probe port, and the battery are detached from the cart, and the display and the console are detached from the body with the probe port and the battery attached, and
a hand-carry style configuration in which the display, the console, the probe port and the battery are each attached and connected to the body.

2. The diagnostic ultrasound apparatus according to claim 1, wherein the display is attachable to and detachable from the cart or the body with a latch structure.

3. The diagnostic ultrasound apparatus according to claim 1, wherein the console is attachable to and detachable from the cart or the body with a latch structure.

4. The diagnostic ultrasound apparatus according to claim 1, wherein the body detached from the display and the console is connectable to the display and the console via a cable or by wireless communication.

5. The diagnostic ultrasound apparatus according to claim 1, wherein the probe port is attachable to the body with an orientation thereof changed.

6. The diagnostic ultrasound apparatus according to claim 1, wherein the cart includes a display cable and a console cable; and
in the cart style configuration, the display and the console are each directly connected to the cart by respective mechanical connections and are electrically connected to the body by the display cable and the console cable.

7. The diagnostic ultrasound apparatus according to claim 1, wherein body includes a wireless communicator; and
in the desktop style configuration, at least one of the display and the console is connected to the body by the wireless communicator.

8. The diagnostic ultrasound apparatus according to claim 1, wherein
the body includes a console connection part for electrically and mechanically connecting the console and the body;
the body includes a display connection part for electrically and mechanically connecting the display and the body; and
in the hand-carry style configuration, the display is electrically and mechanically connected to the body by the display connection part and the console is electrically and mechanically connected to the body by the console connection part.

9. The diagnostic ultrasound apparatus according to claim 8, wherein the cart includes a display cable and a console cable; and
in the cart style configuration, the display and the console are each directly connected to the cart by respective mechanical connections and are electrically connected to the body by the display cable and the console cable.

10. The diagnostic ultrasound apparatus according to claim 9, wherein body includes a wireless communicator; and
in the desktop style configuration, at least one of the display and the console is connected to the body by the wireless communicator.

11. The diagnostic ultrasound apparatus according to claim 8, wherein body includes a wireless communicator; and
   in the desktop style configuration, at least one of the display and the console is connected to the body by the wireless communicator.

\* \* \* \* \*